(12) United States Patent  (10) Patent No.: US 7,434,686 B2
Prindle  (45) Date of Patent: Oct. 14, 2008

(54) AUTO-INJECTOR STORAGE AND DISPENSING SYSTEM

(76) Inventor: Michael Prindle, 64 School St., Arlington, MA (US) 02476

( * ) Notice: Subject to any disclaimer, the term of this patent is extended or adjusted under 35 U.S.C. 154(b) by 402 days.

(21) Appl. No.: 11/009,448

(22) Filed: Dec. 10, 2004

(65) Prior Publication Data

US 2006/0169611 A1    Aug. 3, 2006

(51) Int. Cl.
*B65D 83/10*    (2006.01)
*B65D 25/22*    (2006.01)
*B65D 85/20*    (2006.01)
*A61B 19/02*    (2006.01)

(52) U.S. Cl. ............... 206/364; 206/446; 206/571; 220/478; 312/209

(58) Field of Classification Search ........... 206/364, 206/570, 571, 317, 365, 367, 349, 363, 366, 206/370, 446; 220/476, 478; 211/60.1, 85.13; 248/309.1, 311.2; 312/209; 604/134–136, 604/154–156
See application file for complete search history.

(56) References Cited

U.S. PATENT DOCUMENTS

| | | | | |
|---|---|---|---|---|
| 2,880,864 A | * | 4/1959 | Vassie ............... | 206/364 |
| 3,219,402 A | * | 11/1965 | Holman ............. | 312/209 |
| 3,451,581 A | * | 6/1969 | Warren et al. ...... | 220/4.22 |
| 3,504,787 A | * | 4/1970 | Brockway .......... | 206/570 |
| 4,034,697 A | * | 7/1977 | Russell ............. | 116/100 |
| 5,184,684 A | * | 2/1993 | Kohlman ........... | 169/51 |
| 5,195,595 A | * | 3/1993 | Nakagawa .......... | 169/51 |
| 5,205,408 A | | 4/1993 | Cobb | |
| 5,346,086 A | | 9/1994 | Harris | |
| 5,891,107 A | * | 4/1999 | Carr ................. | 604/259 |
| 5,947,304 A | | 9/1999 | Thorp | |
| 5,950,827 A | | 9/1999 | Odom et al. | |
| 5,960,956 A | | 10/1999 | Langanki et al. | |
| 6,155,420 A | | 12/2000 | Phillips | |
| 6,402,717 B1 | | 6/2002 | Reilly et al. | |
| 6,464,506 B1 | | 10/2002 | Welles | |
| 6,481,808 B2 | | 11/2002 | Cinese | |
| 6,514,280 B1 | | 2/2003 | Gilson | |
| 6,562,008 B1 | | 5/2003 | Reilly et al. | |
| 6,595,362 B2 | | 7/2003 | Penney et al. | |
| 6,622,887 B1 | | 9/2003 | Roediger | |
| 6,736,800 B2 | | 5/2004 | Rindlisbacher | |
| 6,758,338 B2 | * | 7/2004 | Lien ................. | 206/534 |
| 6,936,030 B1 | * | 8/2005 | Pavlik et al. ........ | 604/154 |
| 6,955,259 B1 | * | 10/2005 | Jesse ................. | 206/366 |
| 2004/0188279 A1 | * | 9/2004 | Chen ................. | 206/216 |

* cited by examiner

*Primary Examiner*—Bryon P Gehman
(74) *Attorney, Agent, or Firm*—Edwards Angell Palmer & Dodge LLP; Peter J. Manus

(57) ABSTRACT

A surface-mountable storage system for an auto-injection device. The storage system includes a base and a cover. The base has a back surface adapted to be mounted to a generally vertical surface. A support structure secured to the base releasably holds an auto-injection device on end and adjacent the front surface. The cover has a free edge adapted to be substantially continuously adjacent the base. This allows the cover and base to substantially enclose the auto-injection device when the cover is in a closed position with respect to the base. The storage system also has a latch for securing the cover to the base to allow the cover to move between the closed position and an open position that presents the auto-injection device for removal from the support structure.

14 Claims, 7 Drawing Sheets

AUTO-INJECTOR STORAGE AND DISPENSING SYSTEM

BACKGROUND OF THE INVENTION

1. Field of the Invention

The subject disclosure relates to storage systems for auto-injection devices, and more particularly to storage systems having fixed locations and capable of dispensing auto-injection devices.

2. Background of the Related Art

Many individuals are highly allergic to commonly encountered substances. Examples of common substances which are also common allergens include peanuts, milk, shellfish, latex, and venom from bee stings. Because these and other sources of allergy are prevalent in everyday life, one who is allergic to such a substance cannot predict when they may come in contact with it and have an allergic reaction. When reactions do occur, they can be severe (a condition called "anaphylaxis"); without immediate treatment, anaphylaxis is potentially life-threatening. As a result, many people with known allergies must be continuously ready to treat a reaction.

In order to treat anaphylaxis, many allergy sufferers utilize a device that allows one to quickly administer an appropriate medication, such as epinephrine. These devices are called "auto-injection devices" or "auto-injectors", and are exemplified by the injector sold by DEY L.P. under the registered trademark EpiPen. Auto-injection devices generally contain a single dose of epinephrine and include a retractable needle for quickly injecting the medication intramuscularly. In many cases, allergy sufferers carry an auto-injection device with them at all times.

There are several difficulties associated with the process of constantly carrying an auto-injection device. First, because auto-injection devices include an injection needle and various movable parts, they are relatively fragile and in need of protection from mechanical forces. Second, users must guard against exposing epinephrine to temperature extremes, which can cause it to deteriorate. Third, constantly carrying epinephrine can increase its exposure to UV light, to which it is sensitive. Specifically, epinephrine will oxidize under UV light, turning brown in the process and becoming ineffective. For this reason, most auto-injection devices contain a window through which the color of the contained epinephrine can be visually inspected.

In response to the above issues, several protective cases have been developed for carrying an auto-injection device while shielding it from both mechanical forces and UV radiation. See, for example, U.S. Pat. No. 6,595,362 to Penney and U.S. Pat. No. 5,950,827 to Odom. Both disclosures teach a case that surrounds and completely encloses an auto-injection device, protecting the device from damage and completely shielding it from light. Also, both types of cases are of appropriate size to be easily carried by a user, for example, in a typical pants pocket.

While the prior art protective cases for auto-injection devices, as illustrated by Odom and Penney, have alleviated some of the problems associated with the process of constantly carrying such a device, other difficulties persist. For example, because the prior art protective cases are relatively small and meant to travel with the device, they can be easily misplaced. In places visited regularly, such as a home or office, such cases are often stored out of view, in pockets or drawers, making them easily forgotten when traveling and difficult to locate in times of urgent need. This latter issue is highlighted in situations where the device user, who is often most capable of locating the device, is suffering an anaphylactic reaction and unable either to self-medicate or to describe the device location. Aside from these situations, the typical process by which one carries an auto-injector in anticipation of treating a reaction to a known allergy is useless in cases where the allergy is unknown.

Aside from the above, special problems are encountered when using an auto-injection device in connection with an allergy-suffering child. While many allergy sufferers carry and use auto-injection devices themselves, young children are not capable of such self-medication. Older children, while potentially capable of operating an auto-injector, are likely to damage, misuse, lose, or forget to carry the device. For these reasons, auto-injection devices that are being used to treat child allergies are typically carried by an adult "administrator" (e.g. a parent, teacher, camp counselor, etc.). This practice eliminates issues associated with children carrying auto-injectors; however, it also means that the auto-injection device is not kept immediately with the allergy sufferer, increasing the likelihood that an allergic reaction will occur outside the presence of the device. There is also a risk of forgetting to take an auto-injector when leaving a house. Further, Even at home, school, day care center, camp or the like, an attending adult may be unable to find an auto-injection device. These issues are not addressed by the prior art protective cases.

The above problems can be avoided by creating a storage system for auto-injection devices that holds the devices at a location where anaphylaxis is more likely to occur or where an allergy sufferer is frequently found. Such a system could be used in place of, or in addition to, having each individual sufferer carry a device everywhere with him/her, and would hold devices ready at critical locations, such as a home or office, restaurants, malls, and schools. Ideally, such a storage system would maintain the device in a fixed location and in a manner that makes the device highly visible and easily accessible. However, the accessibility of the storage system would be balanced by an ability to protect the device from damage and/or improper use; this balance becomes critical in cases where an auto-injection device is stored in the presence of children. Aside from the above features, the ideal storage system would also shield the device from exposure to damaging UV light.

The above-described storage system would allow an auto-injection device to be quickly located and accessed in times of need, and would avoid many of the problems associated with carrying individual devices. Further, such a system would facilitate quick treatment even in cases where the allergy was unknown before reaction. In addition, having a storage system that allows the auto-injection device to be visible has several advantages, including allowing visual inspection of the contained epinephrine and reminding users to carry an auto-injection device when traveling. This feature is important because epinephrine's sensitivity to temperature makes storage in a car problematic. However, despite all of these advantages, no storage system like the one proposed exists in the prior art.

SUMMARY OF THE INVENTION

The subject invention is directed to a surface-mountable storage system for an auto-injection device, the system having fixed location and being capable of alternately enclosing an auto-injection device or presenting the device for removal. Such a storage system protects the device from damage or accidental use and maintains such a device in a fixed location and in a manner that makes the device highly visible and easily accessible to adults. Further, the storage system serves to shield the device from UV light while still allowing it to be visible for determining the viability of the contained medication and serving as a reminder to carry a device when traveling.

The storage system includes a base and a cover. The base has a back surface adapted to be mounted to a generally vertical surface. A means is secured to the base for releasably holding an auto-injection device adjacent the front surface. The cover has a free edge adapted to be substantially continuously adjacent the base. This allows the cover and base to substantially enclose the auto-injection device when the cover is in a closed position with respect to the base. The storage system also has means for securing the cover to the base to allow the cover to move between the closed position and an open position that presents the auto-injection device for removal from the releasable holding means.

In one embodiment, the cover has a concave surface and is oriented such that, in the closed position, the concave surface faces the base. The cover is substantially opaque to UV light and at least partially transparent to visible light, allowing objects contained in the system to be viewed. The means for securing the cover to the base is a pivotal attachment configured such that gravitational forces urge the system into the open position. The back surface of the base includes a plurality of mounting holes for affixing the storage system to a generally vertical surface using fasteners. In another embodiment, the back surface of the base is adapted to releasably mount to a substantially vertical support surface, thereby allowing the system to be repeatedly removed from and replaced on the surface.

In one embodiment, the means for temporarily securing an auto-injection device includes a platform extending substantially perpendicularly from the front surface of the base. The platform has an upper surface with a substantially vertical normal direction. An annular wall extends upwardly from the upper surface of the platform. The wall is of suitable height and defines a cavity of suitable diameter for stably containing an auto-injection device while allowing the device to be easily removed. In one embodiment, the platform and annular wall are formed integrally with the base.

It should be appreciated that the present invention can be implemented and utilized in numerous ways. These and other unique features of the system disclosed herein will become more readily apparent from the following description and the accompanying drawings.

BRIEF DESCRIPTION OF THE DRAWINGS

So that those having ordinary skill in the art to which the disclosed invention appertains will more readily understand how to make and use the same, reference may be had to the drawings wherein.

Figure 1:
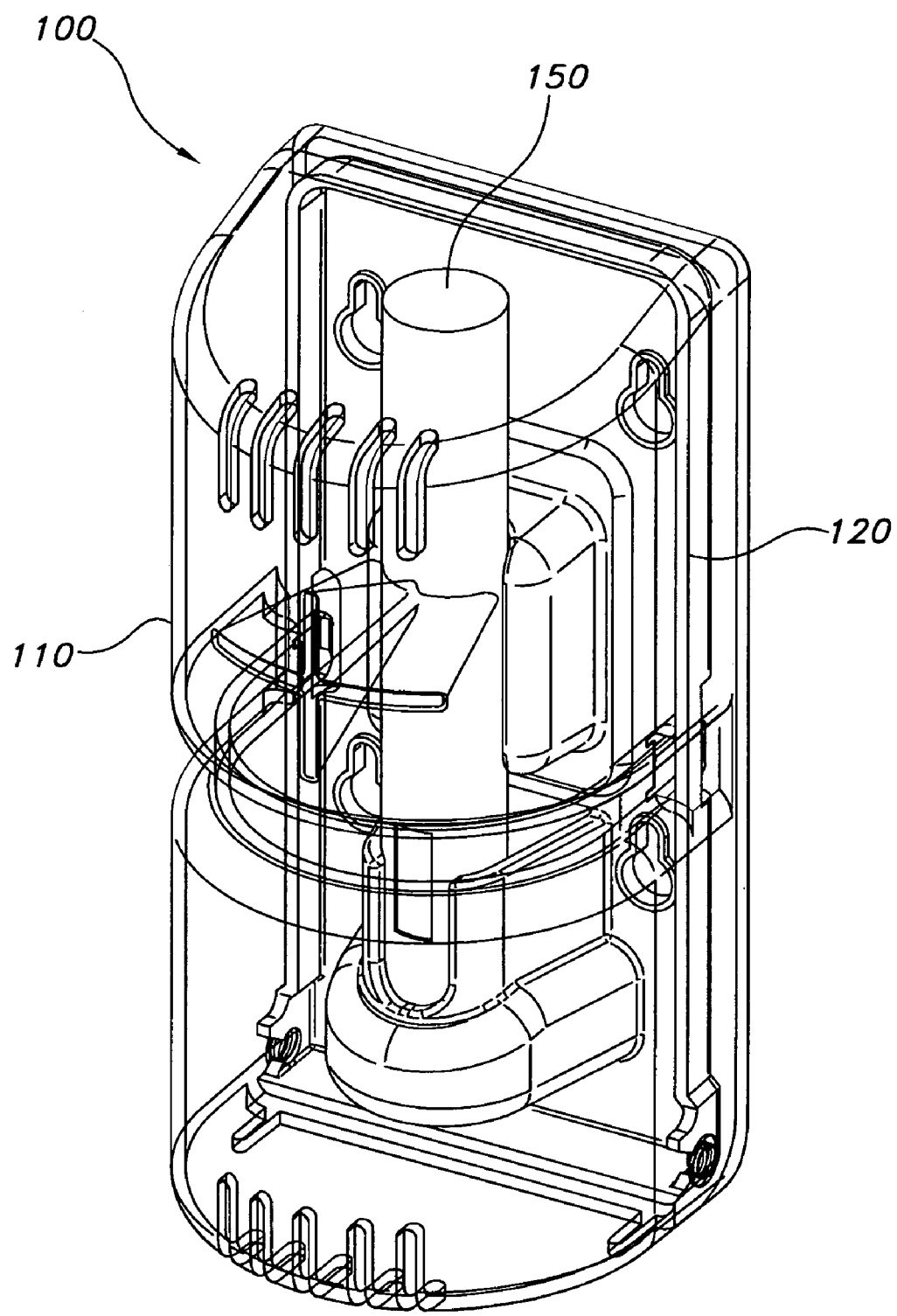
FIG. 1 is a perspective view of a storage system for an auto-injection device in accordance with a preferred embodiment of the subject invention, the storage system being in the closed position.
Figure 7:
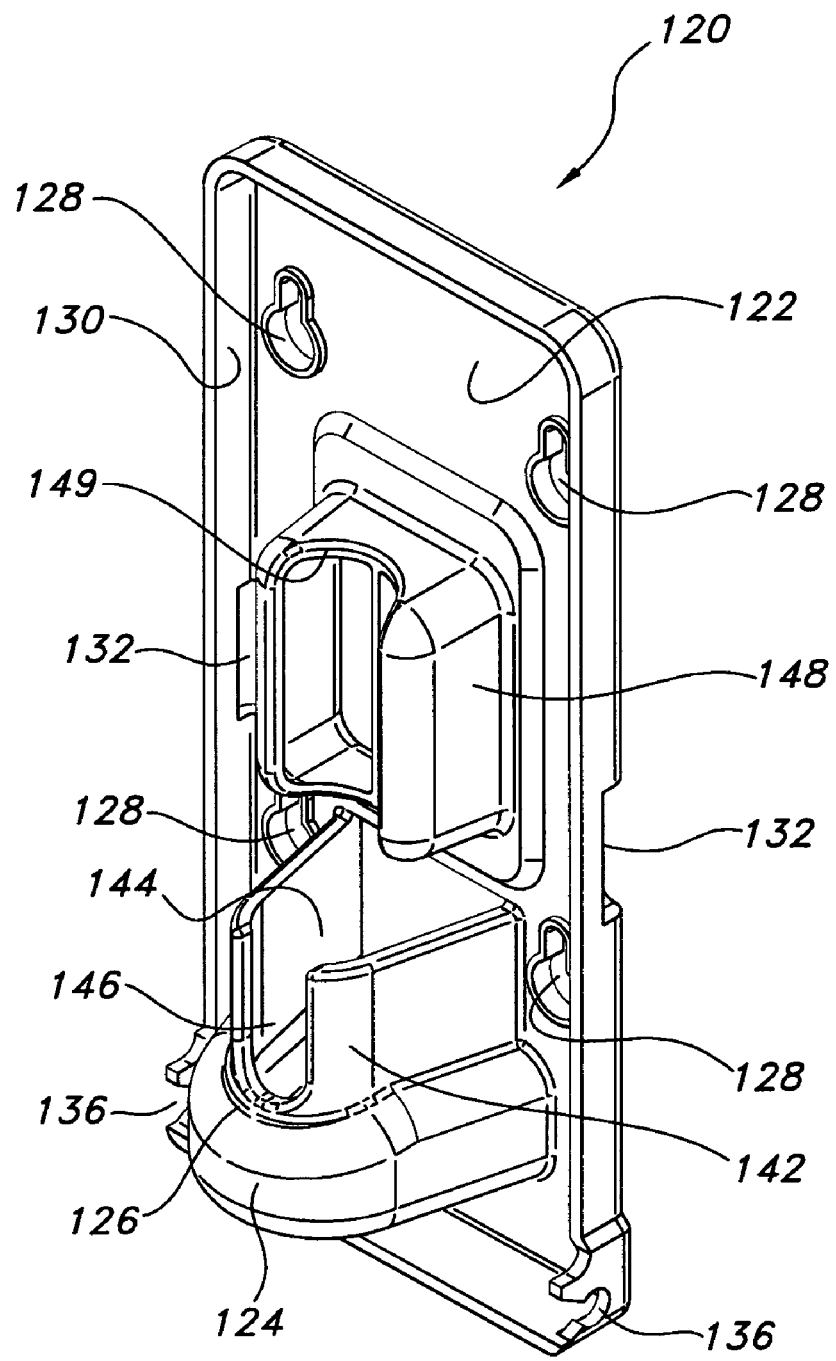

perspective view of the storage system of FIG. 1;

FIG. 7 is a perspective view of the base, platform, and cradle of the storage system of FIG. 1.

DETAILED DESCRIPTION OF PREFERRED EMBODIMENTS

The present invention overcomes many of the prior art problems associated with storing auto-injection devices in preparedness for use. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Figure 2:
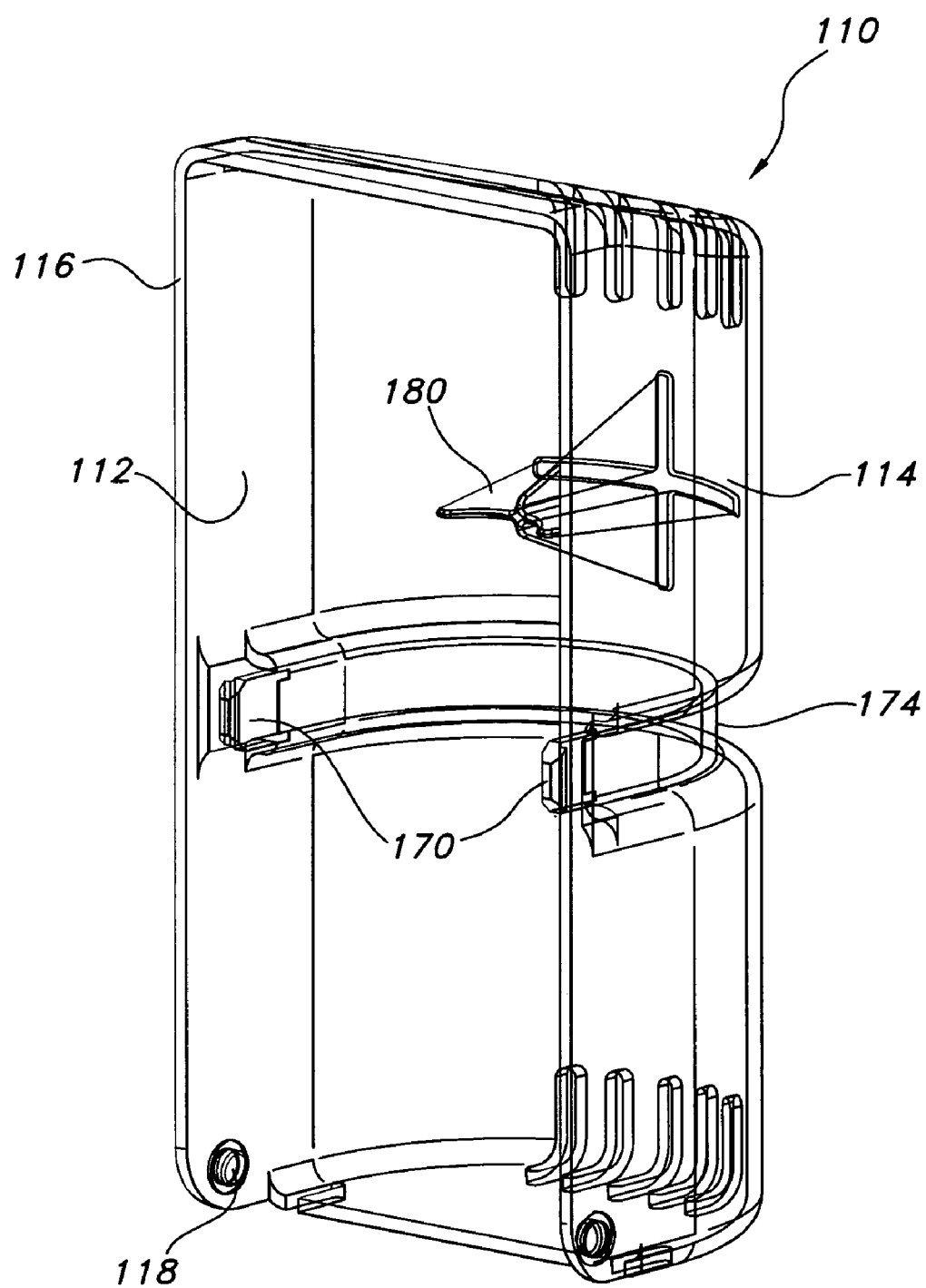
FIG. 2 is a perspective view of the cover of the storage system of FIG. 1.

Referring to FIGS. 1 and 2, there is illustrated a preferred embodiment of an auto-injector storage and dispensing unit (a "storage unit") that is the subject of the present disclosure, the storage unit generally indicated by reference numeral 100. The storage unit 100 has a cover 110 attached to a base 120 in a manner that allows the cover 110 to move with respect to the base 120 (the nature of the attachment and movement is discussed in more detail later). The cover 110 has a concave inner surface 112, an outer surface 114, and a free edge 116. In one configuration of the unit 100, free edge 116 is continuously adjacent to the base 120, allowing the cover 110 and base 120 to form a substantially enclosed volume for containing an auto-injection device 150. This configuration of the storage unit 100, exemplified by FIG. 1, is referred to as "closed". Other shapes and configurations of the cover and base to form the enclosed volume are also possible. For example, the cover may be substantially flat and engage with a concave base, or, both the cover and base may be non-planar.

Figure 3:
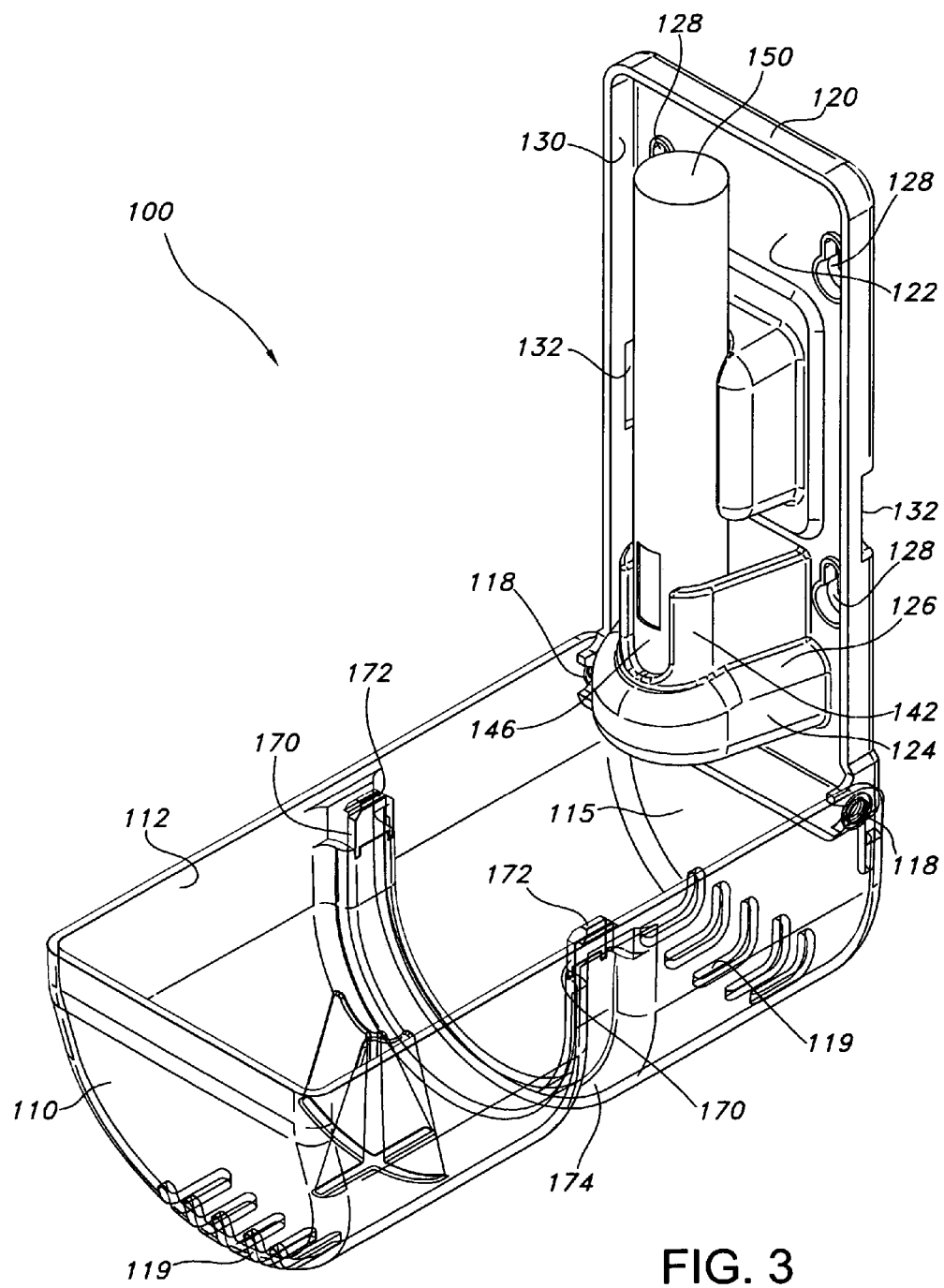
FIG. 3 is a perspective view of the storage system of FIG. 1, the storage system being in the open position to provide access to the auto-injection device.
Figure 4:
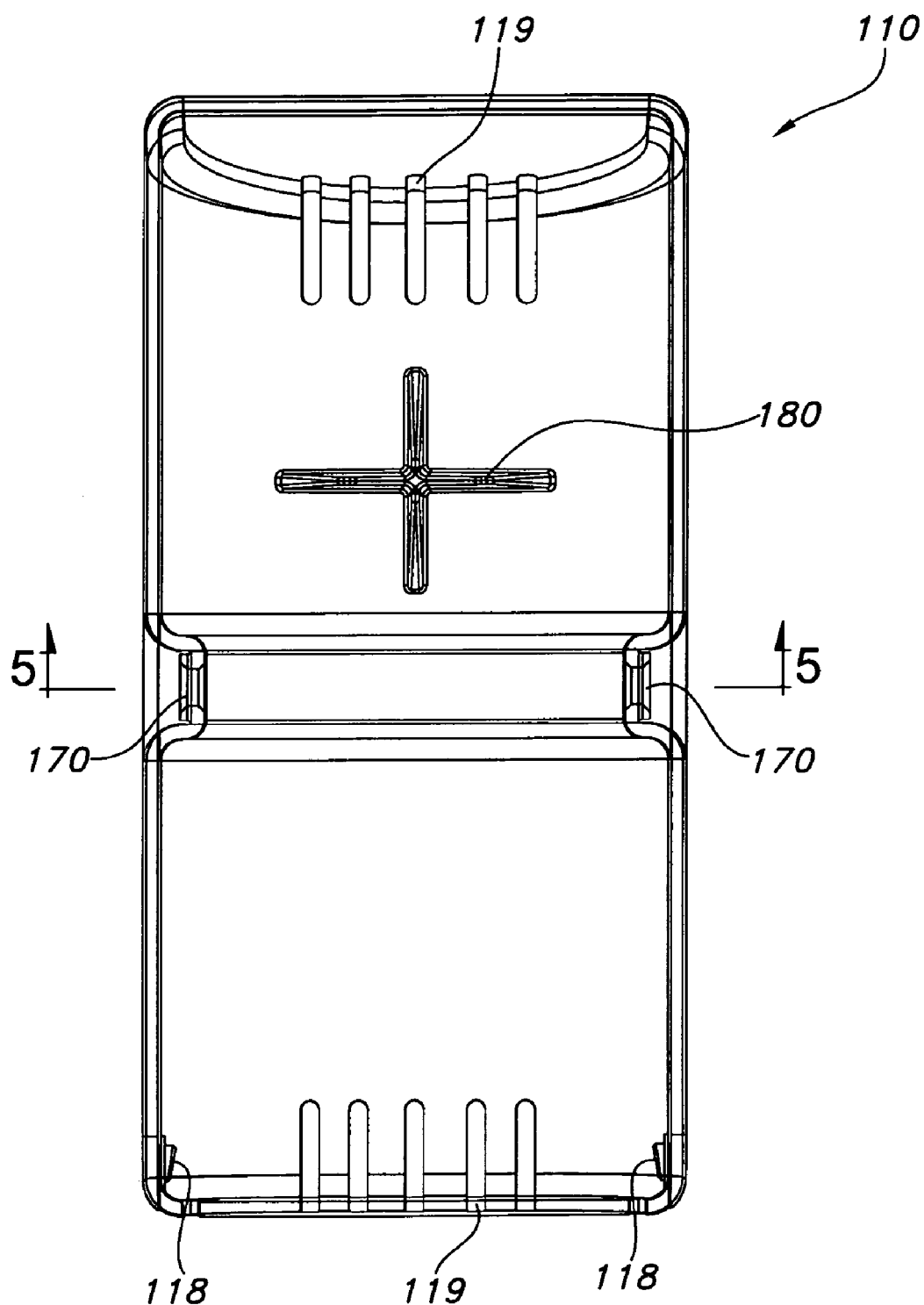
FIG. 4 is a front view of the cover of the storage system of FIG. 1.

Referring to FIGS. 3 and 4, the cover 110 has opposing, integrally-formed protrusions 118 on either side. Protrusions 118 extend into the base 120 by fitting into opposing formed cutouts 136 (FIG. 6), allowing the cover 110 to rotate around the horizontal axis defined by the line connecting the protrusions 118. The cover 110 may thereby rotate away from the base 120 to expose and allow removal of the auto-injection device 150 held adjacent to the front surface 122 of the base 120. This configuration of the storage unit 100, exemplified by FIG. 3, is referred to as "open".

Figure 5:
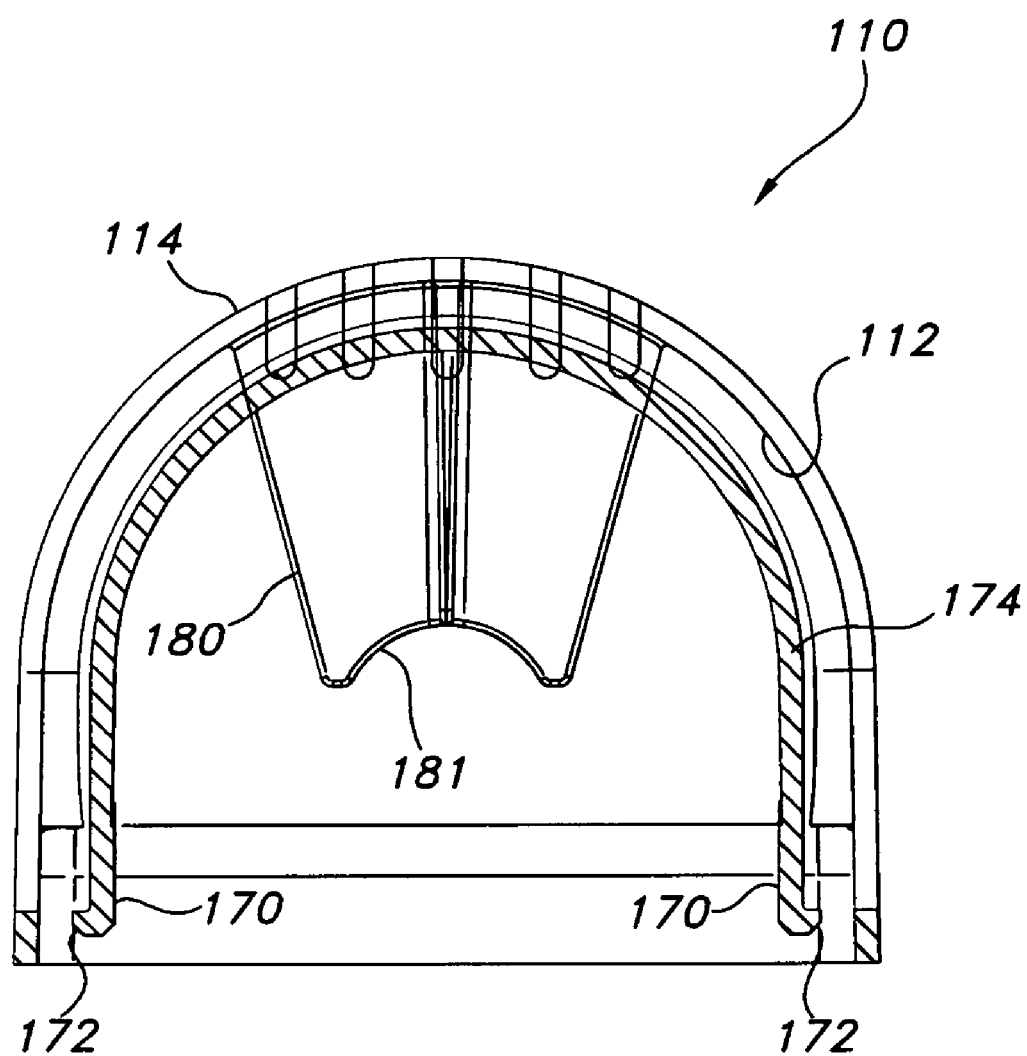
FIG. 5 is a cross-sectional view of the cover of FIG. 4, taken along line 5-5.

Referring to FIGS. 3 and 5, the cover 110 has two latches 170 attached at opposing positions on the inner surface 112 of the cover 110. Each latch 170 has a hook 172, the hooks 172 being directed away from one another. The base 120 (FIG. 3) includes a lip 130 at the perimeter which extends perpendicularly from the front surface 122 of the base 120. Notches 132 are formed in the lip 130 on opposing sides of the base 120. When the cover 110 is in the closed position, the notches 132 engage the latches 170 by catching the hooks 172, thereby holding the cover 110 closed.

In order to open the unit 100, pressure is applied to the outer surface 114 of the cover 110 at locations near the latches 170, thereby elastically compressing the cover 110. A formed groove 174 provides an obvious location for finger and thumb placement during opening, while also serving to strengthen cover 110. The elastic compression forces the latches 170 toward each other, releasing the hooks 172 from the notches 132. The cover 110 is then free to rotate away from the base 120. Preferably, the cover 110 has a thin, shell-like structure, facilitating the deformation process, and is composed of polycarbonate Acetal. The described method of holding the unit 100 closed, requiring both pressure and dexterity to open, discourages children from opening the unit 100 while still allowing easy access for adults.

Figure 6:
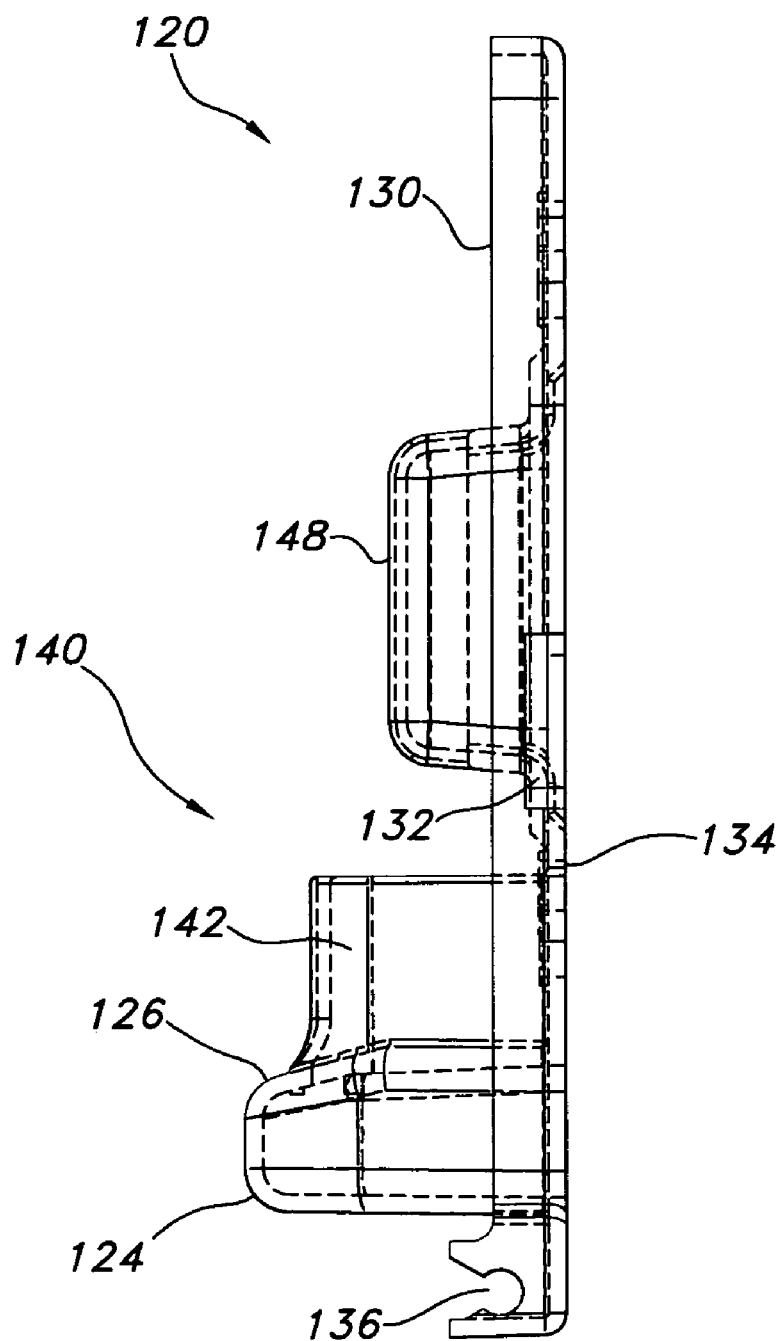
FIG. 6 is a side view of the base of the storage system of FIG. 1.

Referring to FIG. 3, the storage unit 100 is configured such that, when the latches 170 are disengaged from the notches 132 by a user, the cover 110 naturally assumes the open position. This is accomplished by mounting unit 100 to a wall or other substantially vertical support surface, such that the axis of rotation for the cover 110 is located beneath the cover 110 and gravitational forces urge the cover 110 open. Referring to FIGS. 6 and 7, to facilitate such mounting, the back surface 134 of base 120 includes a plurality of holes 128 for engaging screws, nails, or other common fasteners. Preferably, the holes 128 extend completely through the base 120 to the front surface 122, although blind holes are also possible. It is also preferred that the back surface 134 be substantially flat to allow it to sit flush to a wall in a stable configuration. The storage unit 100 is mounted to a surface so that.

Referring to FIG. 3, it is preferred that the cover 110 have an extended bottom portion 115. As the cover 110 rotates away from the base 120 during opening of unit 120, the bottom portion 115 contacts the vertical surface supporting the unit 100, blocking further rotation. By sizing the bottom portion 115 appropriately, the cover 110 remains under the unit 100, extending in a direction generally perpendicular to the vertical support surface. This configuration of the unit 100 has several especially desirable features. First, it allows easy removal of an auto-injection device 150 from unit 100. Second, the cover 110 tends to obstruct the reach of small children, discouraging accidental and/or improper use of the contained auto-injector. Third, the cover 110 acts to catch a device that is accidentally dropped as it is removed from the unit 100.

Referring to FIGS. 3 and 6, a platform 124 extends perpendicularly from the front surface 122, the platform 124 having an upper surface 126. An auto-injection device holder 140, in the form of a support wall 142, extends upwardly from the upper surface 126. Preferably, the platform 124 and support wall 142 are formed integrally with the base 120. For example, the base 120, platform 124, and support wall 142 can all be molded together from plastic, such as polycarbonate Acetal.

Referring to FIG. 7, the support wall 142 defines a cavity 144 of suitable size to receive and hold an auto-injection device 150 on end (FIG. 3) in a vertical position. The height of the support wall 142 is appropriate for stably holding an auto-injector contained therein while still allowing easy removal. Preferably, the wall 142 defines a cut-away 146. The cut-away 146 serves both to facilitate removal of the auto-injector 150 without compromising the stability with which the device 150 is held and to allow more complete viewing of device 150.

The base 120 includes a cradle 148, which projects from front surface 122. Preferably, the cradle 148 is formed integrally with the base 120. The cradle 148 has an edge 149 that is adapted and configured to substantially match the outer surface of an auto-injection device. Referring to FIG. 3, the cradle 148 serves to support the device in an upright position by allowing device 150 to rest against edge 149, thereby facilitating subsequent removal. In conjunction with the cradle 148, the cover 110 includes a support arm 180, preferably formed integrally with the cover 110 (FIG. 5). The support arm 180, like the cradle 148, has an edge 181 contoured to match the outer surface of an auto-injector. The support arm 180 works in tandem with the cradle 148 to surround and support a device when the unit is in the closed position (see FIG. 1).

In a preferred embodiment, the cover 110 is at least partially transparent, allowing an auto-injection device 150 located inside the storage unit 100 to be visible when the unit 100 is closed. The cover 110 may be completely transparent, translucent, or generally opaque but including a transparent window. Preferably, while the cover 110 is somewhat transparent to visible light, it is made opaque to UV light. This can be accomplished, for example, by forming the cover 110 from a material that is transparent to visible light but opaque to UV light, such as specific grade polymers (for example, Optix® CA—75 Clear) or glass.

The ability to see through the cover 110 presents a significant advantage over the prior art auto-injector storage cases. It provides a means for notifying bystanders of the presence and location of an auto-injector. When the unit is situated near an exit of the home or office, the visible auto-injector reminds one to take a device when leaving. It allows the epinephrine contained in the auto-injector to be visually inspected to determine viability. At the same time, the ability of the cover to block UV light protects the epinephrine from being negatively affected by UV exposure, promoting product life.

In a preferred embodiment, illustrated in FIGS. 2 and 6, the cover 110 has a plurality of vent holes 119 that allow air flow between the region inside the unit 110 and the region outside. Such air flow aids in homogenizing the temperature around the auto-injector device. Also, it is preferred that the cover 110 be decorated with markings that make clear the contents of the unit 100 and make the unit 100 as visible as possible. For example, portions of the unit 100 could be painted yellow to indicate that the contents require the use of caution.

While the invention has been described with respect to its preferred embodiments, various modifications will occur to those skilled in the art. For example, while the storage unit 100 has been described as having a cup-like auto-injection device holder 140 that holds a device in a vertical position, other means for holding an auto-injection device are also possible. For example, the auto-injection device may be held by the opposed arms of a C-clip that is attached to the base 120, or, by opposed arms extending perpendicularly from the front surface 122 of the base 120. In both cases, the arms are positioned so as to hold an auto-injection device by applying pressure to the sides of a device inserted between the arms. Alternatively, an annular structure composed of a deformable material can attach to the base. The annular structure has an inner diameter smaller than the outer diameter of an auto-injection device, and when a device is inserted in the annular structure, it compresses the device to hold it. All of the above methods allow for an auto-injection device to be held vertically, horizontally, or in some other position as may be convenient.

Other attachment methods between and relative motions of the cover 110 and the base 120 are also envisioned. For example, the cover 110 may be pivotally connected to the base 120 using, without limitation, protrusions on the base 120 that extend into the holes 118 in the cover 110, a hinge connecting the cover 110 and base 120, fasteners extending through holes in the cover 110 and base 120, or any other known mechanical equivalent for allowing a relative movement of the cover 110 with respect to the base 120. In some embodiments, a hinge may be formed by the meshing of features formed integrally to the cover and base. And, while the cover has been described as rotating around a horizontal axis, the cover 110 may also open by rotating around an axis oriented substantially perpendicularly to the front surface 122 of the base 120, or, around a vertical axis. In still another preferred embodiment, a portion of the cover selectively translates into an open position, for example, by incorporating pins in the cover 110 that slide on a guide tracks on the base 120, or vice versa.

The described unit had a cover that tended to rotate open when not secured shut, due to gravity. The concept wherein the cover naturally tends to an open position can also be realized by having the cover urged open by a spring, latches or some equivalent being used to hold it closed. In another embodiment, the configuration of the cover is bi-stable, such that the cover naturally falls into a closed position until rotated past a certain point, after which the cover naturally falls open.

The storage unit 100 was previously described as being mounted to a vertical support surface using fasteners that engaged through-holes in the base. Alternatively, the storage unit can be mounted by incorporating an adhesive or a magnet in the back surface 134. In still another preferred embodiment, the back surface 134 would be adapted to be releasably mounted to a vertical surface, such that the unit 100 could be easily and repeatedly removed from and replaced on the support surface. For example, male and female portions of hook-and-loop fastener strips (e.g. fasteners commercially available under the tradename VELCRO) can be attached to the base 120 and support surface, respectively. Alternatively, the base could form keyhole-shaped slots which engage the heads of screws or nails to hold the unit 100 on the vertical surface. The unit 100 could then be lifted upward to disengage the screws or nails from the slots and remove the unit 100, or pushed onto the screws or nails and lowered to replace.

The previously described embodiments referred to the use of a specific two-latch system for securing the unit 100 in the closed position. However, a single latch can also be used, or, more than two latches. A latch can be incorporated at locations on the unit 100 other than on the sides, such as on the top. Also, different types of latches can be used, the options being numerous and well-known. It should be noted that many of the means available for securing the unit 100 can be engaged and disengaged without the need to deform the cover, and are independent of the use of a shell-like structure for the cover 110. Also, it is possible to secure the cover without a latch. For example, the cover and base can have portions that overlap and come in sliding contact such that frictional forces prevent them from separating absent an applied force.

The previous descriptions have referred to storage systems for containing a single auto-injection device. However, it is also envisioned that a plurality of devices could be contained in the previously-described embodiments. Also, the described storage systems could include space for safety and use instructions, such that they may be conveniently stored with the devices.

Although the storage system of the subject invention has been described with respect to preferred embodiments, those skilled in the art will readily appreciate that changes and modifications may be made thereto without departing from the spirit and scope of the present invention as defined by the appended claims.

What is claimed is:

1. A storage system for a device that auto-injects a medicine, comprising:
   a base having front and back surfaces, the back surface being adapted to be mounted to a generally vertical surface;
   a releasable holder secured to the base that holds the device adjacent the front surface in a generally vertical orientation when stored;
   a cover having a free edge adapted to be substantially continuously adjacent the base to substantially enclose the device when the cover is in a closed position with respect to the base, said cover being both substantially opaque to UV light and at least partially transparent to visible light and said cover having vents formed therein that create an air flow path around the device; and
   an attachment mechanism that secures the cover to the base to allow the cover to move between the closed position and an open position that presents the device for removal from the releasable holder with the cover extending laterally from the base at a lower portion of the base and positioned and adapted to support a device removed from the releasable holder and dropped.

2. The storage system as recited in claim 1, wherein the attachment mechanism is a pivotal attachment.

3. The storage system as recited in claim 2, wherein the pivotal attachment is configured such that gravitational forces urge the system into the open position.

4. The storage system as recited in claim 2, wherein the pivotal attachment comprises protrusions formed integral to the cover at opposing positions, the protrusions engaging opposing holes in the base to allow the cover to rotate on the protrusions.

5. The storage system as recited in claim 1, further comprising a coating on the surface of the cover that is substantially opaque to UV light.

6. The storage system as recited in claim 5, wherein the coating is substantially transparent to visible light.

7. The storage system as recited in claim 1, wherein the cover has a concave surface and is oriented such that, in the closed position, the concave surface faces the base.

8. The storage system as recited in claim 1, wherein the perimeter of the cover is substantially matched to the outline of the base.

9. The storage system as recited in claim 1, wherein the back surface of the base includes a plurality of mounting holes for affixing the storage system to a generally vertical surface using fasteners.

10. The storage system as recited in claim 1, wherein the releasable holder comprises:
    a platform extending substantially perpendicularly from the front surface of the base, the platform having an upper surface with a substantially vertical normal direction; and
    a support wall extending upwardly from the upper surface of the platform, the wall being of suitable height and defining a cavity of suitable size for stably containing the device while allowing the device to be easily removed.

11. The storage system as recited in claim 10, wherein the platform and support wall are formed integrally with the base.

12. The storage system as recited in claim 1, wherein said attachment mechanism comprises a latch that releasably secures the cover to the base, said latch secured, in part, on said free edge of said cover, and said cover being sized and structured to flex laterally in response to a finger-and-opposed-thumb grip to release said cover to move from said closed position.

13. The storage system as recited in claim 12, wherein said latch includes laterally projecting mating hooks and notches that engage said hooks to secure the said cover to said base in said closed position.

14. The storage system as recited in claim 1, wherein the back surface of the base is adapted to releasably mount to a substantially vertical support surface, thereby allowing the system to be repeatedly removed from and replaced on the substantially vertical support surface.

* * * * *